United States Patent [19]

Meyes

[11] Patent Number: 4,510,137

[45] Date of Patent: Apr. 9, 1985

[54] INSECTION COMPOSITIONS CONTAINING QUINALPHOS AND THIOMETON

[75] Inventor: Peter Meyes, Basel, Switzerland

[73] Assignee: Sandoz Ltd., Basel, Switzerland

[21] Appl. No.: 303,605

[22] Filed: Sep. 18, 1981

Related U.S. Application Data

[63] Continuation of Ser. No. 209,996, Nov. 24, 1980, abandoned, which is a continuation-in-part of Ser. No. 107,427, Dec. 26, 1979, abandoned.

[30] Foreign Application Priority Data

Jan. 2, 1979 [GB] United Kingdom ................. 7900082

[51] Int. Cl.$^3$ ...................... A01N 57/00; A01N 57/26
[52] U.S. Cl. ..................................................... 514/80
[58] Field of Search ................................ 424/200, 216

[56] References Cited

U.S. PATENT DOCUMENTS 3,929,998 12/1975 Lovell ................................. 424/200

OTHER PUBLICATIONS

Chemical Abstracts, 1972-6, Chemical Substance Index-9th Coll.; pp. 28993-28994.

*Primary Examiner*—Leonard Schenkman
*Attorney, Agent, or Firm*—Gerald D. Sharkin; Richard E. Vila

[57] ABSTRACT

A method of combatting insects, particularly in a cotton locus, using quinalphos and thiometon, as well as insecticidal compositions for use in such method.

2 Claims, No Drawings

INSECTION COMPOSITIONS CONTAINING QUINALPHOS AND THIOMETON

This is a continuation of application Ser. No. 209,996, now abandoned filed Nov. 24, 1980, which in turn is a continuation-in-part of Ser. No. 107,427, filed Dec. 26, 1979, now abandoned.

The present invention relates to insecticides.

We have found that the use of (a) the compound of formula I,

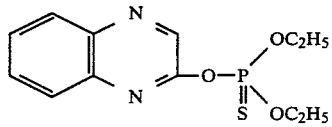

hereinafter referred to by the common name "quinalphos", in association with (b) the compound of formula II,

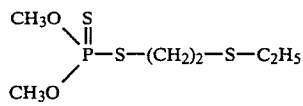

hereinafter referred to by the common name "thiometon",
is particularly effective in combatting insect pests.

The compound quinalphos is a broad spectrum insecticide having contact and stomach activity against pests in a wide range of crops.

Thiometon is also a known insecticide its effectiveness being primarily in the combatting of aphids. We have found, however, that the use of Thiometon in combination with quinalphos surprisingly and substantially enhances the effectiveness of the latter in combating insects.

Accordingly, the invention provides an improved method of combatting insects in a locus, especially in a locus infected by chewing, sucking, biting and mining pests, which comprises applying to the locus, in admixture or separately, an effective aggregate amount of quinalphos and thiometon.

The method of the invention is particularly effective against insects of the orders of Lepidoptera, Homoptera, Coleoptera, Diptera and Thysanoptera, and is especially indicated for combatting insects in vine, vegetables, fruit trees, tea, jute, onion, sugar beet, potatoes, soya, sugar cane, cereals and other field crops and in cotton.

Insect pests that may be successfully combatted with the aid of the method of the invention are i.a. sucking pests, leaf and boll worms in cotton, sucking pests and Lepidopterous larvae in vegetables, sucking pests, Lepidopterous larvae and leaf miners in fruit trees, and the pest complexes in vine and in field crops. Such pests involve the combatting of e.g.

(a) Heliothis sp., such as *Heliothis zea, Heliothis armigera,* Spodoptera spp., such as *Spodoptera littoralis Spodoptera exigua, Earias insulana, Aphis gossypii, Tetranychus telarius, Bemisia Tabaci,* Thrips, Aphids, Jassids and *Pectinophora gossypiella* in cotton, (b) Laspeyresia spp., e.g. *Laspeyresia pomonella, Capua reticulana,* Aphids, *Anarsia Lineatella, Psallus ambiguus,* Operophthera spp., e.g. *Operophthera brumata,* Spilonota spp., e.g. *Spilonota ocellana,* Hedya spp., e.g. *Hedya nubiferana,* Psylla spp., e.g. *Psylla mali, Lyonetia clerkella, Clysia ambiguella, Lobesia botrana, Sparganothis pilleriana,* Pieris spp., e.g., *Pieris rapae,* Mamestra spp., e.g. *Mamestra brassicae, Melittia satyriniformis,* Diaphania spp., *Scirtothrips dorsalis, Leucinodes orbonalis* in fruit trees, vines and vegetables, (c) Heliothis spp. and *Tetranychus telarius* in soya (d) *Leptinotarsa decemlineata, Myzus persicae* and other Aphids in potatoes, (e) *Aphis fabae, Cassida vittata, Pegomyia betae* and and *Myzus persicae* in sugar beet, (f) *Hylemyia antigua* and *Thrips tabaci* in onions, (g) Diatraea spp., e.g. *Diatraea saccharalis,* Aeneolamia spp., e.g. *Aeneolamia varia* in sugar cane, (h) Aphids and Aelia spp., e.g. *Aelia rostrata* in cereals.

According to a preferred aspect of the invention the method is applied in a cotton locus and espcially against the insects *Spodoptera littoralis,* Heliothis spp and *Pectinophora gossypiella.*

The aggregate amount of quinalphos and thiometon to be applied will vary depending upon known factors such as the mode of application, the insects to be combatted, the plant locus, weather conditions, climate factors etc. as well as upon the weight ratio quinalphos:thiometon. Suitable application rates are in general 125 g–1500 g, preferably 250 g–750 g, per hectare, the weight being the total weight of constituents (a) and (b). As already indicated the application rate, however, will depend upon standard factors and the particular crop to be treated; for example, in cotton the preferred application rate is in general somewhat higher e.g. 650 g–875 g per hectare and for example for combatting cotton pests in Egypt, application rates of 750 g–1500 g, preferably 1000–1250 g/ha may be indicated, the application rate relating each case to the total weight of constituents (a) and (b). The weight ratio of quinalphos:thiometon preferably lies in the range of 5:1 to 1:20, especially in the range of 3:1 to 1:10, preferably in the range of 2:1 to 1:4, more preferably 1:1 to 1:4, most preferably 1:1 to 1:3. A particularly interesting weight ratio of guinalphos:thiometon is 1:1.

The invention also provides an insecticidal composition comprising the compound of formula I and the compound of formula II, preferably in the weight ratio as defined above.

The composition of the invention may be formulated in any conventional form, for example in the form of a twin packet, an emulsifiable concentrate, wettable powder or soluble powder, the emulsifiable concentrate form being preferred.

Solid forms may include carriers such as diatomaceous earth, talc, kaolinite, attapulgite, pyrophyllite, artificial mineral fillers based on silicon dioxide and silicates, lime, sodium sulphate decahydrate and plant material carriers such as walnut flour. Adjuvants such as wetting and dispersing agents, e.g. sodium laurylsulphate, sodium dodecyl benzenesulphonate, condensation products of naphthalene sulphonate and formaldehyde, polyglycol ethers and lignin derivatives such as sulphite liquor, may also be included in the case of wettable powders to be applied as an aqueous suspension.

Liquid forms may include non-phytotoxic diluents such as alcohols, glycols, glycolic ethers, aliphatic and aromatic hydrocarbons, e.g. xylene, alkylnaphthalenes and other petroleum distillates, and ketones, e.g. cyclohexanone and isophorone. Adjuvants such as surface active agents, e.g. wetting and emulsifying agents such as polyglycol ethers formed by reaction of alkylene oxides with high molecular weight alcohols, mercaptans or alkyl phenols and/or alkylbenzene sulphonates may be included in emulsion concentrate forms.

Aside from the above mentioned carriers, diluents and adjuvants, other additives such as stabilizing agents, deactivators, surface adhesion improvers, anticorrosives, defoaming agents and pigments may also be included.

the rates of application being 2.2, 2.75 and 3.3 liters Ekalux ®/hectare. The effectiveness of the treatment was assessed by inspection of the crops at intervals from shortly after spraying (zero hour) to 9 days after spraying, the dead and live insects in sample parts of the crop being counted and the results expressed on a scale from 0 to 100, 0 meaning all insects still alive, 100 meaning all insects dead, a figure of 50 meaning half the insects are dead and half alive. The results are set out in the following Table.

TABLE

| TREATMENT | RATE OF APPLICATION per hectare | DAYS AFTER APPLICATION | | | | |
|---|---|---|---|---|---|---|
| | | A/B/C/D/E Zero Hour | A/B/C/D/E 3 days | A/B/C/D/E 5 days | A/B/C/D/E 7 days | A/B/C/D/E 9 days |
| Ekalux alone | 2.2 liters | 50/48/—/—/— | 15/0/—/—/— | 0/0/—/—/— | 0/0/—/—/— | 0/0/—/—/— |
| Ekalux alone | 2.75 liters | 58/56/—/—/— | 24/30/—/—/— | 0/10/—/—/— | 0/0/—/—/— | 0/0/—/—/— |
| Ekalux alone | 3.3 liters | 88/78/—/—/— | 56/44/—/—/— | 20/0/—/—/— | 0/0/—/—/— | 0/0/—/—/— |
| Ekalux/ Ekatin | 2.2. + 2.2 liters | 97.5/100/100/100/100 | 80/100/78/64/70 | 45/35/48/30/56 | 25/10/—/—/— | 0/0/0/0/20 |
| Ekalux/ Ekatin | 1.1 + 3.3 liters | 100/100/100/90/100 | 90/95/90/70/88 | 70/35/72/48/60 | 35/0/—/—/— | 0/0/40/24/40 |

— means that the indicated application or assessment was not carried out.

cluded.

Concentrate forms of the composition according to the invention generally contain from 1 to 90%, preferably 5 to 50% by weight of the constituents (a) and (b).

Application forms of the composition according to the invention generally contain from 0.02 to 90%, preferably from 0.1 to 20% by weight of the constituents (a) and (b).

The invention is illustrated by the following Examples in which all parts and percentages are by weight.

EXAMPLE 1—Emulsifiable Concentrate A 12.5 Parts of quinalphos and 12.5 parts of thiometon are mixed with 20 parts of isooctylphenyl decaglycol ether, 5 parts of xylene. The thus formed concentrate is diluted with water to the desired concentration prior to use.

EXAMPLE 2—Emulsifiable Concentrate B 12.5 Parts of quinalphos and 12.5 parts of thiometon are mixed with 25 parts of isooctylphenyloctaglycol ether, 5 parts of the calcium salt of an alkyl aryl sulphonate and 45 parts of an aromatic petroleum fraction having a boiling point of 210° to 280° C. ($D_{20}$: 0.92). The thus formed concentrate is diluted with water to the desired concentration prior to use.

EXAMPLE 3

Two combined concentrate mixes were prepared, a first by admixing in equal parts by volume Ekalux ® (a commercially available 25% emulsion concentrate of quinalphos) and Ekatin ® (a commercially available 25% emulsion concentrate of thiometon) and a second by admixing 1 part by volume of Ekalux ® with 3 parts by volume of Ekatin ®. The concentrates were diluted with water × 100 and applied separately in Spodoptera littoralis infected cotton crops (five different trials being run A, B, C, D and E) by knapsack sprayer (6 nozzle), the spray from the first concentrate being applied at the rate of 2.2 liters of Ekalux ® and 2.2 liters of Ekatin ® per hectare, the spray from the second concentrate being applied at the rate of 1.1 liters of Ekalux ® and 3.3 liters of Ekatin ® per hectare. Controls were run employing spray liquors formed solely from Ekalux ®, From the table it can clearly be seen that the addition of Ekatin ® (active component thiometon) substantially enhances the insecticidal effect of Ekalux ® (active component quinalphos), which is surprising since it is known that Ekatin ® is practically ineffective against Spodoptera littoralis. The latter is also illustrated by the $LD_{50}$ value found for thiometon against Spodoptera littoralis larvae as given in Example 4 hereinafter; the $LD_{50}$ value of 32.84 ppm found for thiometon indicates an effectiveness which is approximately 24 times inferior than that of quinalphos ($LD_{50}$ = 1.37 ppm).

EXAMPLE 4

The effectiveness of the experimental mixtures against larvae of Spodoptera littoralis was compared with the effectiveness of quinalphos and thiometon used alone.

The larvae originated from a laboratory colony reared on an artificial diet at 25° C., 60% relative humidity and 16 hours photoperiod.

Second instar larvae, weighing 12 mg on the average, were used. Quinalphos, formulated as Ekalux ® and thiometon as Ekatin ®, were serially diluted with tap water in 5 concentrations (dilution factor: 2), either alone or in mixtures. Three mixtures were prepared, differing in their proportions of quinalphos and thiometon, which were 1:1, 1:2 and 1:4, respectively.

Each dilution was sprayed with a spray gun on potted Tradescantia sp. plants, up to the run-off point.

For each concentration, 40 larvae, isolated in plastic compartment cages, were fed ad libitum with the treated leaves of Tradescantia during 7 days. Then the numbers of dead larvae were recorded and expressed as percentage mortalities, corrected, if necessary, by Abbott's formula.

The mortality data were subjected to logit analysis (Berkson J. 1953. J. Amer. Stat. Ass., 48, 595–599) for the estimation of the $LD_{50}$, which is the concentration, expressed in parts per million (ppm) active ingredient, killing 50% of the larvae.

Since these tests were repeated four times, the resulting $LD_{50}$ values were pooled and averaged according to Finney (Finney D. J. 1971. Probit Analysis, Third Edition, Cambridge, at the University Press).

The following $LD_{50}$ values were obtained with the above described procedure:

| Composition | $LD_{50}$ (in ppm) |
|---|---|
| Quinalphos | 1.37 |
| Thiometon | 32.84 |
| Quinalphos/Thiometon 1:1 | 0.39 |
| Quinalphos/Thiometon 1:2 | 0.52 |
| Quinalphos/Thiometon 1:4 | 0.46 |

The method of Abt et al. (Acute Toxicity of Drug Combination: A Method for Evaluating the Interaction of Active Components, Europ. Ges. f. Arzneimittel-Toxikologie, 13. Meeting, Berlin, 7–9.6.1971) was used, in order to detect the presence or the absence of synergism in the mixtures of quinalphos and thiometon.

A factor of synergism, FS, may be calculated, using the following equation:

$$FS = 1/L(A+B)(p(A)/L(A) + p(B)/L(B))$$

where
- $p(A)$ is the proportion of the component A in the mixture,
- $p(B)$ is the proportion of the component B in the mixture,
- with $p(A) + p(B) = 1$
- $L(A)$ and $L(B)$ are the $LD_{50}$ of the components A and B used alone,
- $L(A+B)$ is the $LD_{50}$ of the mixture.

If FS equals 1, the effect is additive, if FS is greater than 1, the effect is synergistic and if FS is smaller than 1, the effect is antagonistic.

The FS calculated for the mixture of quinalphos and thiometon, and given in the table hereinafter are all much greater than 1, thus indicating a high level of synergism for each of the compositions tested:

| Quinalphos/Thiometon | FS |
|---|---|
| 1:1 | 6.74 |
| 1:2 | 7.30 |
| 1:4 | 12.76 |

What is claimed is:

1. An insecticidal composition comprising a non-phytotoxic solid carrier or a non-phytotoxic liquid diluent and in the aggregate an insecticidally effective amount of (a) the compound of formula I

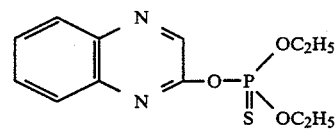

in association with (b) the compound of formula II

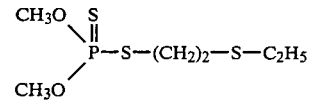

the weight ratio of the compound of the formula I to the compound of the formula II being in the range of from 1:1 to 1:4.

2. A composition according to claim 1, wherein the weight ratio compound of formula I:compound of formula II is in the range 1:1 to 1:3.

* * * * *